US012622939B2

(12) United States Patent
Liu et al.

(10) Patent No.: US 12,622,939 B2
(45) Date of Patent: May 12, 2026

(54) *GANODERMA LUCIDUM* SPORE OIL AND USE THEREOF IN PREPARATION OF ANTI-CANCER-RELATED FATIGUE MEDICAMENTS

(71) Applicant: GUANGZHOU HANFANG PHARMACEUTICAL CO., LTD., Guangzhou (CN)

(72) Inventors: Juyan Liu, Guangzhou (CN); Wendong Xu, Guangzhou (CN); Hongfei Cai, Guangzhou (CN); Jing Li, Guangzhou (CN); Cheng Yuan, Guangzhou (CN); Yaming Han, Guangzhou (CN); Lin Cao, Guangzhou (CN); Shunzhi Tang, Guangzhou (CN); Yukang Mao, Guangzhou (CN); Guocai Wang, Guangzhou (CN); Qin Zhang, Guangzhou (CN)

(73) Assignee: GUANGZHOU HANFANG PHARMACEUTICAL CO., LTD., Guangzhou (CN)

( * ) Notice: Subject to any disclaimer, the term of this patent is extended or adjusted under 35 U.S.C. 154(b) by 311 days.

(21) Appl. No.: 18/415,519

(22) Filed: Jan. 17, 2024

(65) Prior Publication Data
US 2024/0197799 A1  Jun. 20, 2024

Related U.S. Application Data

(63) Continuation-in-part of application No. PCT/CN2022/106599, filed on Jul. 20, 2022.

(30) Foreign Application Priority Data

Jul. 22, 2021 (CN) .......................... 202110830365.7

(51) Int. Cl.
*A61K 36/074* (2006.01)
*A61P 25/00* (2006.01)

(52) U.S. Cl.
CPC ............ *A61K 36/074* (2013.01); *A61P 25/00* (2018.01); *A61K 2236/37* (2013.01); *A61K 2236/51* (2013.01)

(58) Field of Classification Search
CPC .................................................. A61K 36/074
See application file for complete search history.

(56) References Cited

FOREIGN PATENT DOCUMENTS

| | | |
|---|---|---|
| CN | 1907303 | 2/2007 |
| CN | 105079046 A * | 11/2015 |
| CN | 106692213 | 5/2017 |
| CN | 113789214 | 12/2021 |

OTHER PUBLICATIONS

Examination Report No. 1 dated Sep. 23, 2024, from Australian Application No. 2022314013, 4 pages.
Examination Report No. 2 dated Jun. 4, 2025, from Australian Application No. 2022314013, 4 pages.
Examination Report dated May 28, 2025, from Canadian Application No. 3,224,500, 4 pages.
Communication Pursuant Article 94(3) EPC dated Sep. 25, 2024, from European Application No. 22845326.2, 38 pages.
Communication Pursuant Article 94(3) EPC dated Dec. 11, 2025, from European Application No. 22845326.2, 6 pages.
Notice of Refusal dated Nov. 19, 2024, from Japanese Application No. 2024-501638, 4 pages.
Decision of Refusal dated May 27, 2025, from Japanese Application No. 2024-501638, 4 pages.
Saito, Isao et al., "Chapter 11 Column Chromatography," 28 pages.
Tian, Yi-Fu et al., "CMS Analysis of *Ganoderma Lucidum* Spores Oil Extracted by Supercritical $CO_2$," 6 pages.
Zhang, Wenting et al. "Determination of Ganoderma Lucidum Spore Oil Triglycerides by HPLC-ELSD," May 2017, vol. 34, No. 5, 5 pages.
Abulizi, Abudumijiti et al. "Ganoderic acid alleviates chemotherapy-induced fatigue in mice bearing colon tumor," Acta Pharmacologica Sinica, Apr. 29, 2021, 12 pages.
Zhao, Hong et al. "Spore Powder of Ganoderma lucidum Improves Cancer-Related Fatigue in Breast Cancer Patients Undergoing Endocrine Therapy: A Pilot Clinical Trial," 2012, 8 pages, vol. 2012, Hindawi Publishing Corporation.
Lu, Jinxi et al."Study on Chemical Constituents of Ganoderma Lucidum Spore Oil," Jul. 2013, 14 pages, vol. 30, No. 4, Journal of Guangzhou University of Traditional Chinese Medicine.
Tian, Yi-Fu et al. "GC/MS Analysis of Ganoderma Lucidum Spores Oil Extracted by Superficial $CO_2$," China Oils and Fats, vol. 28, No. 09, Sep. 30, 2003, pp. 44-45.
Lu, Jinxi et al. "Study on Chemical Constituents of Ganoderma lucidum Spore Oil," Journal of Guangzhou University of Traditional Chinese Medicine, vol. 30, No. 04, Jul. 20, 2013, 98 pages.
Liu, Guo-Jian et al. "The efficacy enhancing and toxicity reducing of Ganoderma lucidum spore oil emulsion to mice undergoing chemotherapy," Electron J Metab Nutr Cancer, vol. 4, No. 1, Mar. 2017, pp. 60-66.

(Continued)

*Primary Examiner* — Qiuwen Mi
(74) *Attorney, Agent, or Firm* — Haynes and Boone, LLP

(57) ABSTRACT

*Ganoderma lucidum* spore oil and use thereof in the preparation of anti-cancer-related fatigue medicaments are provided. The content of triglycerides in the *Ganoderma lucidum* spore oil is greater than 90%. *Ganoderma lucidum* triterpenoids are not detected. The *Ganoderma lucidum* spore oil is extracted by means of supercritical $CO_2$, eluted with a silica gel column and a mixed solution of petroleum ether-ethyl acetate, concentrated under reduced pressure and vacuum-dried. The *Ganoderma lucidum* spore oil is highly effective in mitigating cancer-related fatigue, has good safety, and can be used in the preparation of medicaments for treating cancer-related fatigue.

7 Claims, 1 Drawing Sheet

(56) References Cited

OTHER PUBLICATIONS

Zhang, Wenting et al. "Determination of Ganoderma Lucidum Spore Oil Triglycerides by HPLC-ELSD," Chinese Journal of Modern Applied Pharmacy, vol. 34, No. 05, May 31, 2017, 4 pages.
Yang, Zhiking et al. "Determination of Liposoluble Components in Ganoderma Lingzhi Spore Powder," Mycosytema, vol. 39, No. 10, Oct. 22, 2020, pp. 1971-1980.

* cited by examiner

GANODERMA LUCIDUM SPORE OIL AND USE THEREOF IN PREPARATION OF ANTI-CANCER-RELATED FATIGUE MEDICAMENTS

CROSS-REFERENCE TO RELATED APPLICATIONS

The present application is a continuation-in-part application of international application PCT/CN2022/106599, filed on Jul. 20, 2022 and entitled "*Ganoderma Lucidum* Spore Oil and Use thereof in Preparation of Drug Counteracting Cancer-related Fatigue", which claims priority to Chinese patent application No. 202110830365.7, filed on Jul. 22, 2021, the contents of which are incorporated herein by reference in their entirety.

TECHNICAL FIELD

The present disclosure relates to the technical field of medicine, and specifically to *Ganoderma lucidum* spore oil and use thereof in the preparation of anti-cancer-related fatigue medicaments.

BACKGROUND ART

Cancer-related fatigue (CRF) is one of the most common symptoms of patients suffering from tumors, which is also the most common side effect in tumor treatment. The National Comprehensive Cancer Network (NCCN) defines cancer-related fatigue as "a distressing, persistent, subjective sense of physical, emotional, or cognitive tiredness or exhaustion related to cancer or cancer treatment that is not proportional to recent activity and interferes with usual functioning". The International Classification of Diseases (ICD) describes the symptoms of cancer-related fatigue as non-specific acratia, weakness, general physical deterioration, lethargy and tiredness. Statistically, more than 75% of tumor patients can show the symptoms of cancer-related fatigue. However, there is neither an exact final conclusion on mechanism researches of the cancer-related fatigue, nor a therapeutic drug for the cancer-related fatigue currently.

Records of diseases related to the "cancer-related fatigue" do not appear in literatures of ancient traditional Chinese medicine, which are usually described as "consumptive diseases". It is recorded in the literature Basic Questions•Comprehensive Theory on Deficiency and Excess "the depletion of essence-qi may bring on deficiency syndrome", which can be deemed as the earliest definition of consumptive disease. It is believed in the literature Synopsis of Prescriptions of the Golden Chamber•Consumptive Diseases that all deficiencies of internal organs and meridians, yin and yang, and qi and blood due to internal lesion caused by overexertion, with a series of symptoms of strain are consumptive diseases. With continuous development of modern traditional Chinese medicine, it is widely believed that the cancer-related fatigue is mostly caused by damage to qi and blood, and body fluid, and injury to qi in zang-fu organs due to emotional disorder, cancer invasion, improper diet and overstrain, etc., which are not recovered for a long time. Therefore, treatment of the cancer-related fatigue is mainly based on the tumor disease per se, and syndrome differentiation and treatment is carried out according to the different deficiency and excess of qi and blood, yin and yang of zang-fu organs. Reinforcing healthy qi to eliminate pathogenic factors is the main treatment principle, with primary reinforcement and supplementary elimination of pathogenic factors. In addition to eliminating causes of fatigue as much as possible, overall regulation should be emphasized.

*Ganoderma lucidum*, as a treasure in traditional Chinese medicine of China, always has the reputation of "magical herb". It can be used for uneasiness, insomnia and palpitation, lung deficiency and cough and asthma, consumptive disease and shortness of breath, and no appetite. *Ganoderma lucidum* spores are ultrafine spores projected from pileus of *Ganoderma lucidum* during the mature stage, as germ cells of *Ganoderma lucidum*, containing all genetically active materials of *Ganoderma lucidum*. Modern pharmacological studies show that *Ganoderma lucidum* spores have anti-tumor and anti-inflammation activity and efficacy of improving immune regulation, reducing blood glucose, reducing blood lipids, anti-hypoxia tolerance, scavenging free radicals, etc. *Ganoderma lucidum* spore oil is a fat-soluble active substance obtained by making *Ganoderma lucidum* spores undergo wall-breaking and supercritical carbon dioxide extraction. Modern researches show that *Ganoderma lucidum* spore oil has anti-tumor activity and efficacy of enhancing immunity, protecting the liver, etc.

It is generally believed in current researches that main effective ingredients of *Ganoderma lucidum* are *Ganoderma lucidum* triterpenoids, and researches on various efficacies of *Ganoderma lucidum* are also more focused on *Ganoderma lucidum* triterpenoids. Accordingly, the researchers usually seek for spore oil with a higher proportion of *Ganoderma lucidum* triterpenoids currently, wherein a content thereof can reach 10-30%. However, there have been no relevant reports for ingredient study and efficacy analysis on other components in the spore oil, such as the most abundant triglycerides. On the other hand, existing researches on the effect of *Ganoderma lucidum* in alleviating fatigue are also concentrated on alleviating physiological fatigue, whereas the effect on pathologic fatigue, particularly cancer-related fatigue, is rarely reported.

SUMMARY

The present disclosure aims at providing *Ganoderma lucidum* spore oil and use thereof in the preparation of anti-cancer-related fatigue medicament. Based on the above reasons and demands, the *Ganoderma lucidum* spore oil is found to have a novel anti-cancer-related fatigue property of, and further new use of *Ganoderma lucidum* spore oil as a medicament is provided, i.e., use in the preparation of a medicament for the treatment or prevention of cancer-related fatigue.

In order to solve the above technical problems, the present disclosure adopts technical solutions as follows:

*Ganoderma lucidum* spore oil, wherein no *Ganoderma lucidum* triterpenoids are detected in the *Ganoderma lucidum* spore oil.

Preferably, a content of triglyceride ingredients is greater than 90% in the *Ganoderma lucidum* spore oil.

In the *Ganoderma lucidum* spore oil in the present disclosure, a content of triglyceride is greater than 90%, a content of ergosterol is 0%-0.5%, wherein the content of ergosterol is not 0%, and no *Ganoderma lucidum* triterpenoids are detected. Currently, most researchers believe that the *Ganoderma lucidum* spore oil has immunity-enhancing and anti-tumor effects due to the abundance of *Ganoderma lucidum* triterpenoids, thus researches on ingredients of the *Ganoderma lucidum* spore oil are mainly focused on enrichment of the *Ganoderma lucidum* triterpenoids. According to current research results, it should be believed that with the decrease of the content of the triterpenoids, various efficacies of the spore oil will decrease or even disappear therewith.

However, upon researches, it is unexpectedly found in the present disclosure that facing pathological fatigue, particularly cancer-related fatigue, when the content of the triglyceride ingredients in the *Ganoderma lucidum* spore oil is greater than 90%, good anti-cancer-related fatigue effect could be achieved. In particular, compared with the spore oil containing the *Ganoderma lucidum* triterpenoids in the prior art, the *Ganoderma lucidum* spore oil of the present disclosure possesses better anti-cancer-related fatigue effect, with significantly improved the effect of relieving mental fatigue and physical fatigue caused by cancer, which was unpredictable and unimaginable before.

A preparation method of the above *Ganoderma lucidum* spore oil, including following steps:

A. making *Ganoderma lucidum* spores subjected to wall-breaking, granulation, drying, and supercritical $CO_2$ extraction to provide a spore oil crude product;

B. dissolving an appropriate amount of silica gel in a mixed solution of petroleum ether and ethyl acetate, preparing a column with the silica gel in the mixed solution to provide an elution column; and C. loading the spore oil crude product onto the elution column, eluting with the mixed solution of petroleum ether and ethyl acetate under normal pressure, collecting and combining eluents, concentrating under reduced pressure to remove solvents, and vacuum-drying, to provide the *Ganoderma lucidum* spore oil.

Upon detection, in the *Ganoderma lucidum* spore oil, the content of triglyceride is greater than 90%, the content of ergosterol is 0%-0.5%, wherein the content of ergosterol is not 0%, and no triterpenoids are undetected. The spore oil substantially free of triterpenoids can be obtained according to this process. On the other hand, the triterpenoids are actually gathered simultaneously as well, and are expected to develop other new products with a higher content of triterpenoids.

Preferably, a ratio of a mass ratio of the spore oil crude product to the silica gel is 1:10-40.

Preferably, in the mixed solution of petroleum ether and ethyl acetate, a volume ratio of petroleum ether to ethyl acetate is 8.5-9.5:0.5-1.5.

Preferably, in the mixed solution of petroleum ether and ethyl acetate, the volume ratio of petroleum ether to ethyl acetate is 9.2:0.8.

Preferably, a ratio of diameter to height of the elution column is 1:10-20.

A method for preventing or treating cancer-related fatigue, comprising administering to a subject a therapeutically effective amount of *Ganoderma lucidum* spore oil, no *Ganoderma lucidum* triterpenoids are detected in the *Ganoderma lucidum* spore oil.

Preferably, a content of triglyceride ingredients is greater than 90% in the *Ganoderma lucidum* spore oil.

Preferably, the *Ganoderma lucidum* spore oil is prepared by following steps:

D. making *Ganoderma lucidum* spores subjected to wall-breaking, granulation, drying, and supercritical $CO_2$ extraction to provide a spore oil crude product;

E. dissolving an appropriate amount of silica gel in a mixed solution of petroleum ether and ethyl acetate, preparing a column with the silica gel in the mixed solution to provide an elution column; and F. loading the spore oil crude product onto the elution column, eluting with the mixed solution of petroleum ether and ethyl acetate under normal pressure, collecting and combining eluents, concentrating under reduced pressure to remove solvents, and vacuum-drying, to provide the *Ganoderma lucidum* spore oil.

Preferably, a mass ratio of the spore oil crude product to the silica gel is 1:10-40.

Preferably, in the mixed solution of petroleum ether and ethyl acetate, a volume ratio of petroleum ether to ethyl acetate is 8.5-9.5:0.5-1.5.

Preferably, in the mixed solution of petroleum ether and ethyl acetate, the volume ratio of petroleum ether to ethyl acetate is 9.2:0.8.

Preferably, a ratio of diameter to height of the elution column is 1:10-20.

Use of the above *Ganoderma lucidum* spore oil in preparation of an anti-cancer-related fatigue medicament.

A medicament comprising the above *Ganoderma lucidum* spore oil, wherein the medicament further comprises a pharmaceutically acceptable carrier.

Preferably, the medicament is one of tablet, capsule, oral absorbent, granule, electuary, pill, pulvis, ointment, pellet, suspension, solution, injection, suppository, cream, spray, drops or patch.

Compared with the prior art, the present disclosure has the following advantageous effects:

By experiments and studies on the ingredients of *Ganoderma lucidum* other than triterpenoids, it is discovered in the present disclosure that the spore oil with greater than 90% of triglyceride and 0%-0.5% of ergosterol has a significant anti-fatigue effect on tumor-bearing mice. Moreover, it is surprisingly discovered that compared with the spore oil containing *Ganoderma lucidum* triterpenoids, the *Ganoderma lucidum* spore oil in the present disclosure significantly improves the effect of relieving mental fatigue and physical fatigue caused by cancer, and has the potential to significantly improve the quality of daily life of cancer patients. Moreover, there is no death or significant weight loss of the animals in the groups of the *Ganoderma lucidum* spore oil in combination with chemotherapeutic agent in the present disclosure, and food intake of the tumor-bearing mice is not affected, indicating that the *Ganoderma lucidum* spore oil has good safety in animals. The *Ganoderma lucidum* spore oil in the present disclosure has the advantageous effects of serving to prepare a medicament for prevention and treatment of cancer-related fatigue, and meanwhile, the gathered and separated triterpenoids are also expected to develop other new products with a higher content of triterpenoids.

DETAILED DESCRIPTION OF EMBODIMENTS

Figure 1:
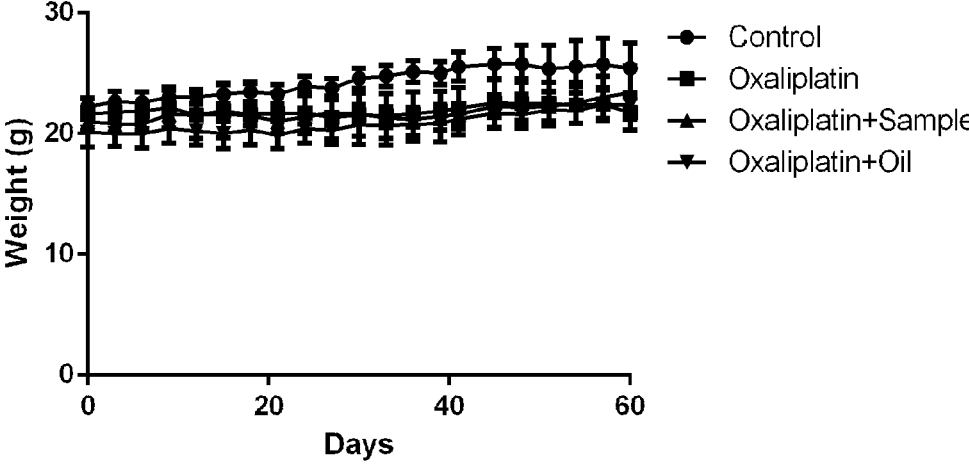
FIG. 1 is a statistical chart of mean values of body weights of mouse models tumor-transplanted with human gastric cancer variable with experimental time in Effect Example 4.

The present disclosure is further described in detail below with reference to drawings and specific examples in order to better illustrate the objectives, technical solutions, and advantages of the present disclosure.

Example 1

*Ganoderma lucidum* spore oil, obtained by following steps: making *Ganoderma lucidum* spores subjected to wall-breaking, granulation, drying, and supercritical $CO_2$ extraction, followed by adsorption and separation by a silica gel column. A separation process was as follows: dissolving an appropriate amount of silica gel in a mixed solution of petroleum ether and ethyl acetate in a volume ratio of 9.2:0.8, preparing a column with the silica gel in the mixed solution, wherein the ratio of diameter to height of the column prepared was 1:10, loading the spore oil onto the column, wherein the mass ratio of the spore oil to the silica gel was 1:28, eluting the spore oil with the petroleum ether and ethyl acetate in a volume ratio of 9.2:0.8 under normal pressure, collecting and combining eluents, concentrating under reduced pressure to remove solvents, and vacuum-drying, to provide a spore oil sample.

In the *Ganoderma lucidum* spore oil, the content of triglyceride was greater than 90%, the content of ergosterol was 0%-0.5%, wherein the content of ergosterol is not 0%, and no *Ganoderma lucidum* triterpenoids were detected.

Example 2

*Ganoderma lucidum* spore oil, obtained by following steps: making *Ganoderma lucidum* spores subjected to wall-breaking, granulation, drying, and supercritical $CO_2$ extraction, followed by adsorption and separation by a silica gel column. A separation process was as follows: dissolving an appropriate amount of silica gel in a mixed solution of petroleum ether and ethyl acetate in a volume ratio of 9.2:0.8, preparing a column with the silica gel in the mixed solution, wherein the ratio of diameter to height of the column prepared was 1:13, loading the spore oil onto the column, wherein the mass ratio of the spore oil to the silica gel was 1:28, eluting the spore oil with the petroleum ether and ethyl acetate in a volume ratio of 9.2:0.8 under normal pressure, collecting and combining eluents, concentrating under reduced pressure to remove solvents, and vacuum-drying, to provide a spore oil sample.

In the *Ganoderma lucidum* spore oil, the content of triglyceride was greater than 90%, the content of ergosterol was 0%-0.5%, wherein the content of ergosterol is not 0%, and no *Ganoderma lucidum* triterpenoids were detected.

Example 3

*Ganoderma lucidum* spore oil, obtained by following steps: making *Ganoderma lucidum* spores subjected to wall-breaking, granulation, drying, and supercritical $CO_2$ extraction, followed by adsorption and separation by a silica gel column. A separation process was as follows: dissolving an appropriate amount of silica gel in a mixed solution of petroleum ether and ethyl acetate in a volume ratio of 9.2:0.8, preparing a column with the silica gel in the mixed solution, wherein the ratio of diameter to height of the column prepared was 1:15, loading the spore oil onto the column, wherein the mass ratio of the spore oil to the silica gel was 1:28, eluting the spore oil with the petroleum ether and ethyl acetate in a volume ratio of 9.2:0.8 under normal pressure, collecting and combining eluents, concentrating under reduced pressure to remove solvents, and vacuum-drying, to provide a spore oil sample.

In the *Ganoderma lucidum* spore oil, the content of triglyceride was greater than 90%, the content of ergosterol was 0%-0.5%, wherein the content of ergosterol is not 0%, and no *Ganoderma lucidum* triterpenoids were detected.

Example 4

*Ganoderma lucidum* spore oil, obtained by following steps: making *Ganoderma lucidum* spores subjected to wall-breaking, granulation, drying, and supercritical $CO_2$ extraction, followed by adsorption and separation by a silica gel column. A separation process was as follows: dissolving an appropriate amount of silica gel in a mixed solution of petroleum ether and ethyl acetate in a volume ratio of 9.2:0.8, preparing a column with the silica gel in the mixed solution, wherein the ratio of diameter to height of the column prepared was 1:15, loading the spore oil onto the column, wherein the mass ratio of the spore oil to the silica gel was 1:30, eluting the spore oil with the petroleum ether and ethyl acetate in a volume ratio of 9.2:0.8 under normal pressure, collecting and combining eluents, concentrating under reduced pressure to remove solvents, and vacuum-drying, to provide a spore oil sample.

In the *Ganoderma lucidum* spore oil, the content of triglyceride was greater than 90%, the content of ergosterol was 0%-0.5%, wherein the content of ergosterol is not 0%, and no *Ganoderma lucidum* triterpenoids were detected.

Example 5

*Ganoderma lucidum* spore oil, obtained by following steps: making *Ganoderma lucidum* spores subjected to wall-breaking, granulation, drying, and supercritical $CO_2$ extraction, followed by adsorption and separation by a silica gel column. A separation process was as follows: dissolving an appropriate amount of silica gel in a mixed solution of petroleum ether and ethyl acetate in a volume ratio of 9.3:0.7, preparing a column with the silica gel in the mixed solution, wherein the ratio of diameter to height of the column prepared was 1:15, loading the spore oil onto the column, wherein the mass ratio of the spore oil to the silica gel was 1:35, eluting the spore oil with the petroleum ether and ethyl acetate in a volume ratio of 9.3:0.7 under normal pressure, collecting and combining eluents, concentrating under reduced pressure to remove solvents, and vacuum-drying, to provide a spore oil sample.

In the *Ganoderma lucidum* spore oil, the content of triglyceride was greater than 90%, the content of ergosterol was 0%-0.5%, wherein the content of ergosterol is not 0%, and no *Ganoderma lucidum* triterpenoids were detected.

Example 6

*Ganoderma lucidum* spore oil, obtained by following steps: making *Ganoderma lucidum* spores subjected to wall-breaking, granulation, drying, and supercritical $CO_2$ extraction, followed by adsorption and separation by a silica gel column. A separation process was as follows: dissolving an appropriate amount of silica gel in a mixed solution of petroleum ether and ethyl acetate in a volume ratio of 9.2:0.8, preparing a column with the silica gel in the mixed solution, wherein the ratio of diameter to height of the column prepared was 1:15, loading the spore oil onto the column, wherein the mass ratio of the spore oil to the silica gel was 1:33, eluting the spore oil with the petroleum ether and ethyl acetate in a volume ratio of 9.2:0.8 under normal pressure, collecting and combining eluents, concentrating under reduced pressure to remove solvents, and vacuum-drying, to provide a spore oil sample.

In the *Ganoderma lucidum* spore oil, the content of triglyceride was greater than 90%, the content of ergosterol was 0%-0.5%, wherein the content of ergosterol is not 0%, and no *Ganoderma lucidum* triterpenoids were detected.

Example 7

*Ganoderma lucidum* spore oil, obtained by following steps: making *Ganoderma lucidum* spores subjected to wall-breaking, granulation, drying, and supercritical $CO_2$ extraction, followed by adsorption and separation by a silica gel column. A separation process was as follows: dissolving an appropriate amount of silica gel in a mixed solution of petroleum ether and ethyl acetate in a volume ratio of 9.0:1.0, preparing a column with the silica gel in the mixed solution, wherein the ratio of diameter to height of the column prepared was 1:17, loading the spore oil onto the column, wherein the mass ratio of the spore oil to the silica gel was 1:35, eluting the spore oil with the petroleum ether and ethyl acetate in a volume ratio of 9.0:1.0 under normal pressure, collecting and combining eluents, concentrating under reduced pressure to remove solvents, and vacuum-drying, to provide a spore oil sample.

In the *Ganoderma lucidum* spore oil, the content of triglyceride was greater than 90%, the content of ergosterol was 0%-0.5%, wherein the content of ergosterol is not 0%, and no *Ganoderma lucidum* triterpenoids were detected.

Example 8

*Ganoderma lucidum* spore oil, obtained by following steps: making *Ganoderma lucidum* spores subjected to wall-breaking, granulation, drying, and supercritical $CO_2$ extraction, followed by adsorption and separation by a silica gel column. A separation process was as follows: dissolving an appropriate amount of silica gel in a mixed solution of petroleum ether and ethyl acetate in a volume ratio of 9.5:0.5, preparing a column with the silica gel in the mixed solution, wherein the ratio of diameter to height of the column prepared was 1:10, loading the spore oil onto the column, wherein the mass ratio of the spore oil to the silica gel was 1:10, eluting the spore oil with the petroleum ether and ethyl acetate in a volume ratio of 9.5:0.5 under normal pressure, collecting and combining eluents, concentrating under reduced pressure to remove solvents, and vacuum-drying, to provide a spore oil sample.

In the *Ganoderma lucidum* spore oil, the content of triglyceride was greater than 90%, the content of ergosterol was 0%-0.5%, wherein the content of ergosterol is not 0%, and no *Ganoderma lucidum* triterpenoids were detected.

Example 9

*Ganoderma lucidum* spore oil, obtained by following steps: making *Ganoderma lucidum* spores subjected to wall-breaking, granulation, drying, and supercritical $CO_2$ extraction, followed by adsorption and separation by a silica gel column. A separation process was as follows: dissolving an appropriate amount of silica gel in a mixed solution of petroleum ether and ethyl acetate in a volume ratio of 8.5:1.5, preparing a column with the silica gel in the mixed solution, wherein the ratio of diameter to height of the column prepared was 1:20, loading the spore oil onto the column, wherein the mass ratio of the spore oil to the silica gel was 1:40, eluting the spore oil with the petroleum ether and ethyl acetate in a volume ratio of 8.5:1.5 under normal pressure, collecting and combining eluents, concentrating under reduced pressure to remove solvents, and vacuum-drying, to provide a spore oil sample.

In the *Ganoderma lucidum* spore oil, the content of triglyceride was greater than 90%, the content of ergosterol was 0%-0.5%, wherein the content of ergosterol is not 0%, and no *Ganoderma lucidum* triterpenoids were detected.

Effect Example 1

Anti-fatigue effect of *Ganoderma lucidum* spore oil on mouse models tumor-transplanted with human lung cancer
1. Experimental Animals Nude mice, SPF level, half females and half males, totally 32. Feeding environment: SPF-level animal house nude mouse room, free food intake, 12 h light/12 h darkness, animal house at ambient temperature of 16-26° C. and relative humidity of 40%-70%.
2. Experimental Materials Test sample 1 (commercially available *Ganoderma lucidum* spore oil containing *Ganoderma lucidum* triterpenoid ingredients), and test sample 2 (*Ganoderma lucidum* spore oil obtained by the process in the present disclosure, wherein the triglyceride content was greater than 90%, the ergosterol content was 0%-0.5%, wherein the content of ergosterol is not 0%, and the no *Ganoderma lucidum* triterpenoids were detected). The test samples were respectively formulated with corn oil into solutions at corresponding concentrations before administration. The solutions were formulated when using.

Cell strain: human lung cancer NCI-H460 cell strain.
3. Experimental Method (1) Construction of nude mouse tumor-transplanted models: after NCI-H460 cells were cultured to a required number, they were digested and counted, and then inoculated, by 0.15 ml per mouse, into the nude mice near upper right limb for modeling (blank control group was not inoculated). When tumor volume grew to about 100 mm$^3$, the nude mice were randomly divided into four groups: blank control group (Control), tumor model group (Model), group of test sample 1 (Sample 1), and group of test sample 2 (Sample 2). 8 mice were included in each group, half females and half males.

(2) Administration method

Route of administration: intragastric administration of the test samples 1 and 2 and corn oil.

Weekly administration frequency: the test samples 1 and 2 and corn oil were administered once a day.

Administration cycle: the test samples 1 and 2 and corn oil were administered continuously for 4 weeks.

Administration dosage: test sample 10 mL/kg

Administration volume: 0.1 mL/10 g body weight, i.e., 10 mL/kg, for administration.

(3) Tail suspension test

The tail suspension test was carried out for tumor-bearing mice on day 28 after the administration. Mouse tails (2 cm from tail tip) were stuck on a tester with tape, so that the mice were hang upside down. The mice kept struggling in order to overcome abnormal position. The state in which the mice completely stopped struggling and were stationary was recorded as "immobile". Accumulated immobile time of the mice in 6 min was recorded.
4. Experimental Results The results are shown in Table 3. On day 28 of the administration, mean tail suspension immobile time of the tumor-bearing mice in the tumor model group is significantly longer than that of the blank control group, and the two groups have a significant difference upon comparison (P<0.05); mean tail suspension immobile time of the tumor-bearing mice in the group of test sample 1 and the group of test sample 2 is significantly shorter than that in the tumor model group, and the two groups have a significant difference compared with the tumor model group (P<0.05); mean tail suspension immobile time of the tumor-bearing mice in the group of test sample 2 is significantly shorter than that in the group of test sample 1, and the two groups still have a significant difference upon comparison (P<0.05).

TABLE 3

Influence of *Ganoderma lucidum* Spore Oil
on Behaviors of Female Tumor-bearing Mice

| Group | Mean Tail Suspension Immobile Time (s) |
|---|---|
| Blank Control Group | 54.39 ± 31.25* |
| Tumor Model Group | 177.85 ± 42.30 |
| Group of Test Sample 1 | 110.77 ± 68.31* |
| Group of Test Sample 2 | 51.46 ± 21.89*, # |

Notes:
compared with the tumor model group, *P < 0.05; and compared with the group of test sample 1, #P < 0.05.

In the tail suspension test, since the mice were in abnormal positions, the mice would keep struggling, as long as mentally and physically allowed, in an attempt to overcome the abnormal position. Namely, if the mice did not feel weary throughout, the tail suspension immobile time would be 0 theoretically. On the contrary, if the mice felt mentally or physically weary during struggling, they would stop struggling and start to rest, which period would be recorded. Thus, the longer the mean tail suspension immobile time is, the more severe the mice felt mentally and physically weary in this process.

The tail suspension test results show that the administration of the test sample 1 and the test sample 2 can significantly shorten the tail suspension immobile time of the tumor-bearing mice, and the test sample 2 can further significantly shorten the tail suspension immobile time of the tumor-bearing mice, and even reach a level of normal tumor-free mice (the blank control group), compared with the test sample 1. This indicates that the *Ganoderma lucidum* spore oil without triterpenes prepared in the present disclosure, compared with the spore oil containing the *Ganoderma lucidum* triterpenoids, has a more significant anti-fatigue effect on the tumor-bearing mice, can even reach a level of a cancer-free situation, and significantly improves the effect of relieving mental fatigue and physical fatigue caused by cancer.

Based on this, only the *Ganoderma lucidum* spore oil without triterpenoids prepared in the present disclosure was used for further effect experiments and safety experiments of drugs in combination.

Effect Example 2

Anti-fatigue effect of *Ganoderma lucidum* spore oil on mouse models tumor-transplanted with liver cancer
1. Experimental Animals
Kunming mice, SPF level, 40 females. Feeding environment: SPF-level animal house mouse room, free food intake, 12 h light/12 h darkness, animal house at ambient temperature of 16-26° C. and relative humidity of 40%-70%.

2. Experimental Materials
Test sample (*Ganoderma lucidum* spore oil obtained by the process in the present disclosure), which was formulated with corn oil into a solution at corresponding concentration before administration. The solution should be formulated when using. Chemotherapeutic agent (cyclophosphamide), Batch No.: 8D231A, 200 mg/bottle, manufactured by Baxter Oncology GmbH, formulated with normal saline into a solution at corresponding concentration before administration. The solutions were formulated when using.
Cell strain: mouse H22 liver cancer cell strain.
3. Experimental Method
i. Construction of mouse tumor-transplanted models: after H22 cells were cultured to a required number, they were digested and counted, and then inoculated, by 0.1 ml per mouse, into the mice near upper right limb for modeling. When a tumor volume grew to about 100 mm³, the mice were randomly divided into four groups: blank control group (Control), cyclophosphamide group (CTX), *Ganoderma lucidum* spore oil (GLSO), and cyclophosphamide+*Ganoderma lucidum* spore oil group (CTX+GLSO). 10 mice were included in each group.
ii. Administration method
Route of administration: intragastric administration of *Ganoderma lucidum* spore oil; and tail vein administration of cyclophosphamide.
Weekly administration frequency: once a day, 5 days of continuous administration followed by 2 days of rest.
Administration cycle: continuous administration for 3 weeks.
Administration dosage: *Ganoderma lucidum* spore oil 10 ml/kg; cyclophosphamide 30 mg/kg.
Administration volume: 0.1 mL/10 g body weight, i.e., 10 mL/kg, for administration.
iii. Exhaustive swimming test
Tumor-bearing mice were subjected to exhaustive swimming test on day 13 and day 20 after the administration, respectively. The tumor-bearing mice were placed to swim in a swimming case, in which the water depth was not less than 30 cm and the water temperature was 25±1 ° C. The time from starting to swim to exhaustion of the tumor-bearing mice was recorded. Limbs of each tumor-bearing mouse were kept in motion throughout the experiment. If the tumor-bearing mouse floated on water surface and did not move its limbs, water could be agitated with a wooden stick near the mouse. The tumor-bearing mouse was judged to be exhausted when it sank below the water surface for 10 s and could not float by itself. When average swimming time exceeded 360 s, the swimming time was counted as 360 s.
4. Experimental Results
The results are shown in Table 1. On day 13 and day 20 of the administration, after the administration of the *Ganoderma lucidum* spore oil alone, the average swimming time of the tumor-bearing mice is significantly longer than that of the model group, and the two groups have a significant difference upon comparison (P<0.05); on day 13 and day 20 of the administration, after combined administration of the cyclophosphamide and the *Ganoderma lucidum* spore oil, the average swimming time of the tumor-bearing mice is significantly longer than that of the model group, and the two groups have a significant difference upon comparison (P<0.05).

TABLE 1

Influence of *Ganoderma lucidum* Spore Oil
on Behaviors of Female Tumor-bearing Mice

| | Average Swimming Time (s) | |
| --- | --- | --- |
| Group | 13 d of administration | 20 d of administration |
| Model Control Group | 196.78 ± 92.12 | 131.89 ± 71.05 |
| Chemotherapeutic Agent Group | 264.88 ± 123.28 | 182.00 ± 73.32 |
| *Ganoderma lucidum* Spore Oil Group | 343.14 ± 136.23* | 231.14 ± 105.88* |
| Chemotherapeutic Agent + *Ganoderma lucidum* Spore Oil Group | 382.13 ± 226.08* | 284.00 ± 74.85* |

Note:
compared with the model control group, *P < 0.05

The results show that the *Ganoderma lucidum* spore oil can significantly prolong the exhaustive swimming time of the tumor-bearing mice, indicating that the *Ganoderma lucidum* spore oil in the present disclosure has a significant anti-fatigue effect on liver cancer tumor-bearing mice.

Effect Example 3

Anti-fatigue effect of *Ganoderma lucidum* spore oil on mouse models tumor-transplanted with human gastric cancer 1. Experimental Animals Nude mice, SPF level, 40 females. Feeding environment: SPF-level animal house mouse room, free food intake, 12 h light/12 h darkness, animal house at ambient temperature of 16-26° C. and relative humidity of 40%-70%.

2. Experimental Materials

Test sample (*Ganoderma lucidum* spore oil obtained by the process in the present disclosure), which was formulated with corn oil into a solution at corresponding concentration before administration. The solution should be formulated when using. Chemotherapeutic agent (Oxaliplatin), Batch No.: 190911AM, 50 mg/bottle, manufactured by Jiangsu Hengrui Pharmaceuticals Co., Ltd., formulated with normal saline into a solution at corresponding concentration before administration. The solutions were formulated when using.

Cell strain: human gastric cancer MNK45 cell strain.

3. Experimental Method i. Construction of nude mouse tumor-transplanted models: after MNK45 cells were cultured to a required number, they were digested and counted, and then inoculated, by 0.1 ml per mouse, into the nude mice near upper right limb for modeling. When a tumor volume grew to about 100 mm³, the nude mice were randomly divided into four groups: model control group (Control), chemotherapeutic agent group (Oxaliplatin), chemotherapeutic agent+test sample group (Oxaliplatin+Sample), and chemotherapeutic agent+ corn oil group (Oxaliplatin+Oil). 10 mice were included in each group.

ii. Administration method

Route of administration: intragastric administration of the test sample and corn oil; and tail vein administration of the oxaliplatin.

Weekly administration frequency: the test sample and corn oil were administered once a day, 5 days of continuous administration followed by 2 days of rest. The Oxaliplatin was administered twice a week, i.e., on the day of D1 day and the day of D4.

Administration cycle: the chemotherapeutic agent was administered for 6 weeks; and after 6 weeks administration of the test sample and corn oil, the administration was continued until the test ended.

Administration dosage: the test sample 10 ml/kg; the oxaliplatin 2 mg/kg.

Administration volume: 0.1 mL/10 g body weight, i.e., 10 mL/kg, for administration.

iii. Exhaustive swimming test

Tumor-bearing mice were subjected to exhaustive swimming test on day 37 and day 49 after the administration, respectively. The tumor-bearing mice were placed to swim in a swimming case, in which water depth was not less than 30 cm and a water temperature was 25±1° C. The time from starting to swim to exhaustion of the tumor-bearing mice was recorded. Limbs of each tumor-bearing mouse were kept in motion throughout the experiment. If the tumor-bearing mouse floated on water surface and did not move its limbs, water could be agitated with a wooden stick near the mouse. The tumor-bearing mouse was judged exhausted when it sank below the water surface for 10 s and could not float by itself. When average swimming time exceeded 360 s, the swimming time was counted as 360 s.

4. Experimental Results

The results are shown in Table 2. On day 37 of the administration, after the administration of the chemotherapeutic agent of oxaliplatin and the *Ganoderma lucidum* spore oil, the average swimming time of the tumor-bearing mice is significantly longer than that in the model group, and the two groups have a significant difference upon comparison (P<0.05); one week after the chemotherapeutic agent administration was stopped, i.e., on day 49 of the administration, the average swimming time of the tumor-bearing mice is still significantly longer than that in the model group, and the two groups have a significant difference upon comparison (P<0.05).

TABLE 2

Influence of *Ganoderma lucidum* Spore Oil
on Behaviors of Female Tumor-bearing Mice

| | Average Swimming Time (s) | |
| --- | --- | --- |
| Group | 37 d of administration | 49 d of administration |
| Model Control Group | 168.67 ± 113.32 | 253.83 ± 111.72 |
| Chemotherapeutic Agent Group | 174.67 ± 107.15 | 290.17 ± 81.24 |
| Chemotherapeutic Agent + Test Sample Group | 306.33 ± 74.95* | 360.00 ± 0.00* |
| Chemotherapeutic Agent + Corn oil Group | 285.33 ± 101.83 | 284.17 ± 87.85 |

Note:
compared with the model control group, *P < 0.05

The results show that the administration of the test sample can significantly prolong the exhaustive swimming time of the tumor-bearing mice, indicating that the *Ganoderma lucidum* spore oil in the present disclosure has a significant anti-fatigue effect on the tumor-bearing mice.

Effect Example 4

Research on In Vivo Safety of *Ganoderma lucidum* Spore Oil

1. *Ganoderma lucidum* Spore Oil does not Affect the Body Weight of the Tumor-Bearing Mice The results are shown in FIG. 1. The *Ganoderma lucidum* spore oil in combination with oxaliplatin does not result in significant weight loss of the tumor-bearing mice.

Figure 2:
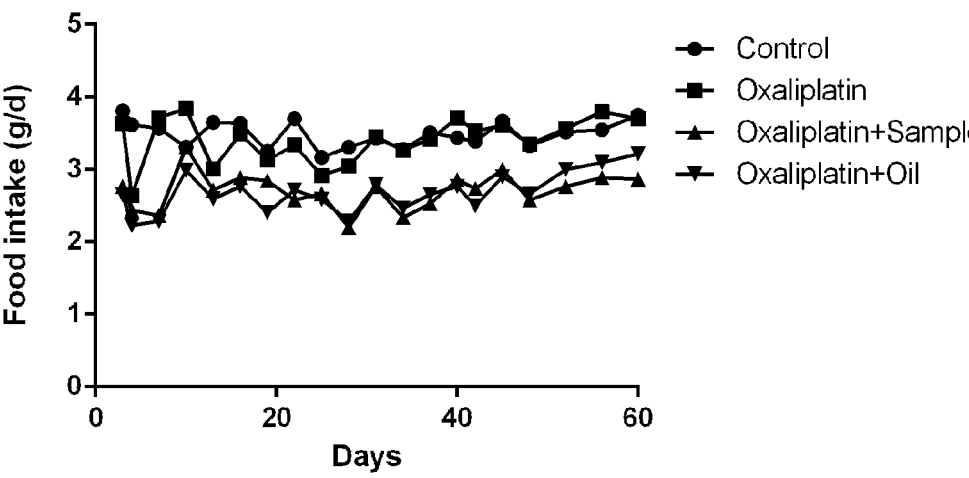
FIG. 2 is a statistical chart of mean values of daily food intake of the mouse models tumor-transplanted with human gastric cancer variable with experimental time in Effect Example 4.

2. *Ganoderma lucidum* Spore Oil does not Affect Food Intake of the Tumor-Bearing Mice The results are shown in FIG. 2. The *Ganoderma lucidum* spore oil in combination with oxaliplatin does not result in significant reduction of food intake of the tumor-bearing mice.

To sum up, the *Ganoderma lucidum* spore oil in the present disclosure has a significant anti-fatigue effect on the tumor-bearing mice. Moreover, there is no death or significant weight loss of the animals in the group of *Ganoderma lucidum* spore oil in combination of chemotherapeutic agent in the present disclosure, and the food intake of the tumor-bearing mice is not affected, indicating that the *Ganoderma lucidum* spore oil has good safety in animals. The *Ganoderma lucidum* spore oil in the present disclosure has the advantageous effects of serving to prepare a medicament for prevention and treatment of cancer-related fatigue.

What is disclosed above is only for preferred examples of the present disclosure, and certainly the scope of right of the present disclosure should not be limited thereto. Therefore, equivalent changes made in accordance with the claims of the present disclosure are still within the scope covered by the present disclosure.

What is claimed is:

1. A method for reducing the incidence of or treating cancer-related fatigue, comprising administering to a subject in need thereof a therapeutically effective amount of *Ganoderma lucidum* spore oil, wherein no *Ganoderma lucidum* triterpenoids are detected in the *Ganoderma lucidum* spore oil.

2. The method according to claim 1, wherein a content of triglyceride ingredients is greater than 90% in the *Ganoderma lucidum* spore oil.

3. The method according to claim 1, wherein the *Ganoderma lucidum* spore oil is prepared by following steps:

A. making *Ganoderma lucidum* spores subjected to wall-breaking, granulation, drying, and supercritical $CO_2$ extraction to provide a spore oil crude product;

B. dissolving an appropriate amount of silica gel in a mixed solution of petroleum ether and ethyl acetate, preparing a column with the silica gel in the mixed solution to provide an elution column; and C. loading the spore oil crude product onto the elution column, eluting with the mixed solution of petroleum ether and ethyl acetate under normal pressure, collecting and combining eluents, concentrating under reduced pressure to remove solvents, and vacuum-drying, to provide the *Ganoderma lucidum* spore oil.

4. The method according to claim 3, wherein a mass ratio of the spore oil crude product to the silica gel is 1:10-40.

5. The method according to claim 3, wherein in the mixed solution of petroleum ether and ethyl acetate, a volume ratio of petroleum ether to ethyl acetate is 8.5-9.5:0.5-1.5.

6. The method according to claim 5, wherein in the mixed solution of petroleum ether and ethyl acetate, the volume ratio of petroleum ether to ethyl acetate is 9.2:0.8.

7. The method according to claim 3, wherein a ratio of diameter to height of the elution column is 1:10-20.

* * * * *